United States Patent [19]

Feitelson

[11] Patent Number: 4,994,389

[45] Date of Patent: Feb. 19, 1991

[54] PROMOTER-PROBE PLASMID FOR ANALYSIS OF TRANSCRIPTIONAL REGULATION

[75] Inventor: Jerald S. Feitelson, Englewood, N.J.

[73] Assignee: American Cyanamid Company, Stamford, Conn.

[21] Appl. No.: 24,291

[22] Filed: Mar. 10, 1987

[51] Int. Cl.$^5$ .................. C12N 1/20; C12N 15/00
[52] U.S. Cl. ...................... 435/252.35; 435/172.3; 435/320.1; 935/29; 935/75
[58] Field of Search ................ 435/61, 172.1, 172.3, 435/320, 243, 253, 886, 252.3, 252.31–252.35, 69.1, 71.1, 71.2; 935/29, 75, 79, 84, 76

[56] References Cited

U.S. PATENT DOCUMENTS 4,468,462  8/1984  Malin et al. ................. 435/253

FOREIGN PATENT DOCUMENTS 0118367  12/1984  European Pat. Off. ......... 435/172.3

OTHER PUBLICATIONS

Bibb et al.; Mol. Gen. Genet. 187: 265 (1982).
McKenney et al.; in *Gene Amplification and Analysis*, vol. 2, Chirikjian et al. (ed.), 1981, Elesevier/North-Holland, New York, pp. 383–415.
Ward, et al., Mol. Gen. Genet. 203, 468–478 (1986).
Horinouchi, et al., J. Bact., 162: pp. 406–412 (1985).
Feitelson, et al., J. Nat. Prod. 49:988–994 (1986).

*Primary Examiner*—James Martinell

[57] ABSTRACT

The invention provides a recombinant plasmid that is capable of inducing the expression of a brown pigment. The plasmid is a pARC1 plasmid into which has been inserted DNA which includes a transcriptional terminator and a polylinker sequence.

2 Claims, 2 Drawing Sheets

PL (POLYLINKER) SEQUENCE:

BglII  PstI  HindIII  SphI  PstI  SalI  XbaI BamHI  SmaI  KpnI SstI  EcoRI  BglII  BclI
AGATCTGCAGCCAAGCTTGCATGCCTGCAGGTCGACTCTAGAGGATCCCCGGGTACCGAGCTCGAATTCCCCAGATCTGATCA

PROMOTER-PROBE PLASMID FOR ANALYSIS OF TRANSCRIPTIONAL REGULATION

BACKGROUND OF THE INVENTION

1. FIELD OF THE INVENTION

This invention relates to a novel plasmid and as novel microorganism containing the plasmid. The novel plasmid is useful for assaying promoter activity in Streptomyces as well as for increasing the yield of antibiotic fermentations.

2. DESCRIPTION OF THE PRIOR ART

In the prior art (Horinouchi, et al., J. Bacteriol. 162, 406-412 (1985)) the promoter-probe plasmid vector pARC1 has been constructed. This plasmid vector has a unique BamHI cloning site that allows chromogenic identification of transcriptional control signals in *Streptomyces lividans*. Multi-copy promoter-probe plasmid vectors for Streptomyces have been described by Ward, et al. MGG 203 p.468-478 (1986) These promoter-probe plasmids may be used to isolate and characterize Streptomycetes promoters.

Horinouchi, et al. used the disclosed technique to isolate promoter containing fragments involved in the transcriptional regulation of gene expression. The disclosed plasmid allows for the direct detection of fragments involved in the transcriptional regulation of gene expression by the activation of brown pigment encoding genes in Streptomyces. In addition, promoters which function late in the life cycle can be readily detected. The significant shortcoming of the pARC1 plasmid, in the analysis of gene expression signals, is the difficulty of reisolating the promoter containing fragments for subsequent analysis. Restriction enzyme sites are remote from the unique BamHI cloning site which makes it difficult to reisolate the cloned fragment. The basal level of brown pigment production in the intact vector is low and makes it difficult or impossible to detect low promoter activity.

Another class of prior art promoter-probe vectors utilizes the activation of a promoterless drug resistance gene. These methods are selective and require the early and constitutive expression of the cloned promoter in order to achieve significant levels of resistance. An example of a construct is PIJ486. Ward, et al. supra. This construct employs the aminoglycoside phosphorase transfer gene (aph) as a indicator system. This plasmid contains a transcriptional terminator originally isolated from phage fd in order to eliminate transcriptional readthrough from the vector into the aph gene. This plasmid also has a polylinker region containing the sites for several useful restriction enzymes.

The requirement for early and constitutive promoter activity precludes the detection of promoters which only express late in the life cycle of the organism.

The present invention comprises the construction of a novel plasmid that comprises a pARC1 parent into which is inserted a transcriptional terminator and a polylinker sequence. This recombinant plasmid may be used to identify, isolate and characterize DNA fragments which contain functional promoters involved in the initiation and control of RNA synthesis. In addition, these DNA fragments are useful in making high yield Streptomyces strains for producing antibiotics. Examples of such products that are produced from Streptomyces are described in U.S. Pat. No. 4,468,462 which is incorporated by reference.

It has now been found that a Streptomyces plasmid, pCLL34 may be constructed from the previously disclosed plasmids pARC1 and pIJ446.

Accordingly, it is a primary object of this invention to provide a Streptomyces promoter-probe vector for the analysis of transcriptional regulation.

It is also an object of this invention to provide a novel plasmid that may be utilized to increase the yield of an antibiotic from a Streptomyces such *Streptomyces aureofaciens, Streptomyces noursei* or *Streptomyces aureus*.

BRIEF DESCRIPTION OF THE DRAWINGS

The structure and the method for the preparation of the recombinant bacterial plasmids of the present invention are illustrated in the specification when taken with the accompanying drawing wherein:

FIG. 2 shows the sequence of the polylinker PL.

DETAILED DESCRIPTION OF THE INVENTION

EXAMPLE

Figure 1:
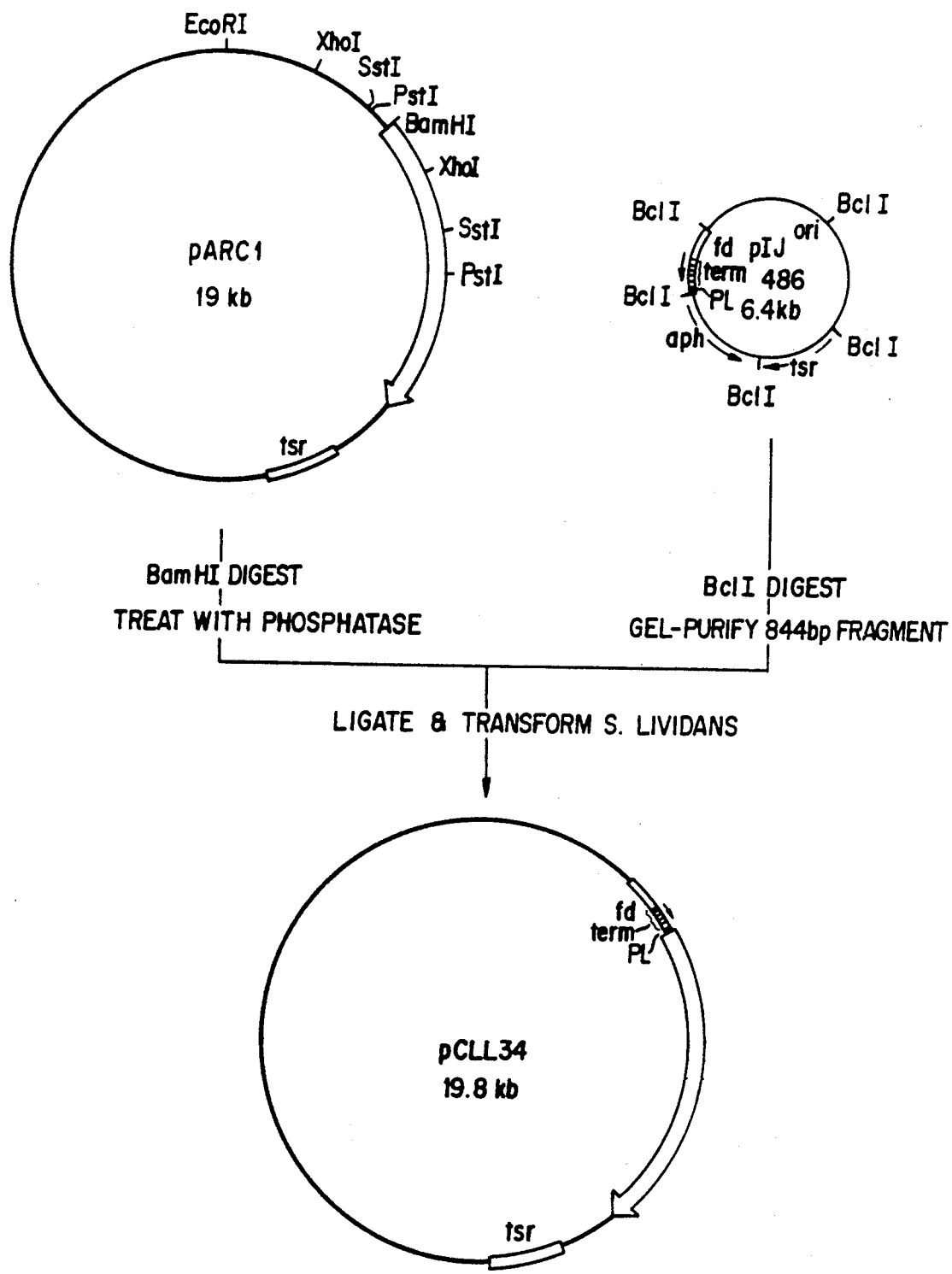
FIG. 1 is a flow chart that shows how pCLL34 is prepared from pARC1 and pIJ486.

4 μg of pIJ486 DNA is digested with 36.4 units BclI at 50° C. for 30 minutes in a reaction volume of 100 microliters containing 6.0 mM Tris-HCl; 100 mM/l $MgCl_2$, 6 mmol mercaptoethanol, 7 mmol/l Triton X-100 0.01% (v/v) pH 8.0. The reaction products are loaded into a 1.5% low melting point agarose gel and subjected to electrophoresis at 100 V and 25 mamps for 1.75 hours. The gel is stained with ethidium bromide 0.5 μg/ml for 15 minutes and the fastest migrating band (844 bp) is sliced out of the gel under 310 nm UV light. The DNA is recovered from the gel slice (693 mg) by melting at 70° C. for 5 min. Then 9.7 ml of LS buffer (0.2 M NaCl; 20 mM tris-HCl pH 7.5; 1.0 mM EDTA) is added and heating continued for 25 min. at 70° C. to ensure complete gel dissolution. The solution is cooled to 37° C. and passed through an equilibrated Schlechter & Schuell Elutip-d. After rinsing with 5 ml of LS buffer, the DNA is eluted with 2×200μl of HS buffer (1.0 M NaCl; 20mM tris-HCl pH 7.5, 1.0 mM EDTA) and precipitated with 800μl of ethanol at −20° C. overnight. The DNA is recovered by centrifugation (14,000 xg.; 5 min. at 4° C.) and resuspended in 20μl of TE buffer (10 mM tris-HCl pH 8.0; 1 mM ETDA).

20μg of pARC1 DNA is digested in a reaction volume of 200μl, containing 10mM tris-HCl pH 8.0; 100mM NaCl; 5 mM $MgCl_2$; 1 mM 2-mercaptoethanol and 40 units of BamHI at 37° C. for 2 hours. This procedure yields 3.16 pmoles of DNA termini. After phenol-chloroform extraction and chloroform extraction, DNA is recovered by ethanol precipitation and resuspended in 80 μl of TE buffer and incubated with 0.316 units of calf intestine alkaline phosphatase in a reaction mixture containing 100 mM tris-HCl; 10 mM $MgCl_2$; 50 mM NaCl and 100μg/ml of bovine serum albumin at 37° C. for 30 min. The reaction is terminated by heating at 70° C. for 10 min. The DNA is extracted with phenol-chloroform and chloroform, recovered by ethanol precipitation and resuspended in 200μl TE buffer to a final concentration of 100 μg/ml.

0.25μg of dephosphorylated pARC1/BamHI is ligated to the gel purified 844 bp PIJ486/BclI in a reaction volume of 25 ul containing 30 mM tris-HCl, pH 7.5; 6 mM $MgCl_2$; 10 mM dithiothreitol; 50μg/ml bovine serum albumin, 1 mM ATP and 1 unit of T4 DNA ligase at 15° C. for 40 hours. The ligation is monitored by agarose gel electrophoresis to detect the formation of the hybrid plasmid.

The ligation mixture is introduced by transformation into protoplasts of *Streptomyces lividans* TK54 SLP2−, SLP3−, leu-2; his-2; spc$^r$. A 1 ml aliquot of frozen *Streptomyces lividans* TK54 is thawed rapidly and divided into 0.75 ml and 0.25 ml portions. Protoplasts are recovered by centrifugation (14,000 xg for 10 sec. at 22° C.). The supernatants are then discarded. 5μl of the ligation mixture are added to the larger pellet of protoplasts immediately followed by 0.5 ml of 25% polyethylene glycol (PEG-1000) in T buffer (Thompson, et al., J. Bacteriol. 151, 668 14 677 (1982)) and mixed thoroughly by trituration and plated on 4 R2YE plates containing 50μg/ml of leucine and 50μg/ml histidine. The plates are incubated for 20 hours at 30° C. and overlaid with 3 ml of Difco soft nutrient agar containing 500μg/ml of thiostrepton. After 48 hrs. the transformants are counted resulting in 183 thiostrepton resistant transformants. Nine clones are randomly selected with a TK54 [pARCl] control and screened for plasmid DNA by the rapid method of Kieser (Plasmid 12, 19 14 36 (1984)) to confirm the presence of the desired 844 bp insert. Inserts are detected in both orientations as determined by the EcoRI fragmentation pattern. Clone 1 with the polylinker clockwise from the terminator yields EcoRI fragments of 16.71 kb and 3.41 kb Clone 5 with the terminator clockwise from the polylinker region yields EcoRI fragments of 17.54 kb and 2.31 kb EcoRI and BamHI double digest of the parental pARCl plasmid, without any insert, yields fragments of 16.7 kb and 2.3 kb The plasmid of Clone 1 was designated pCLL34 and its map appears in FIG. 1.

FUNCTIONAL EXPRESSION OF PROMOTER IN pCLL34

In J. Natural Prod. 49 No. 6 pp. 988–994 (1986), a description appears of a series of promoter containing fragments isolated in pARCl. One of the isolates (pr 7A) contained a 0.16 kb insert which activated the very early and strong expression of brown genes. The purified 0.16 kb fragment, flanked by Sau3A sites, is cloned into the unique BamHI site of pCLL34 using a procedure that is analogous to the ligation techniques set forth hereinabove. The ligation mixture is introduced by transformation into protoplasts of *Streptomyces lividans* TK54 using the general procedures set forth hereinabove. Brown pigment production was expressed at the same level and at the same time as by the same insert that is cloned in the parental plasmid pARCl. The transformed *Streptomyces lividans* has been deposited at the American Type Culture Collection as ATCC 67,346. This result demonstrates that the additional thirty five base pairs of polylinker sequences between the BamHI site and the start of the brown genes in pCLL34 do not interfere with gene expression. The fact that a polylinker is present between the fd terminator and the brown genes, makes it possible to assay a great variety of DNA fragments for promoter activity. In addition, it also greatly facilitates the characerization and subsequent manipulation of promoters cloned into the polylinker region of pCLL34.

I claim:
1. The recombinant plasmid pCLL34.
2. A transformed *Streptomyces lividans* host cell containing the plasmid pCLL34.

* * * * *